US007700112B2

(12) United States Patent
Garone et al.

(10) Patent No.: US 7,700,112 B2
(45) Date of Patent: Apr. 20, 2010

(54) FSH BETA MUTANTS THAT ARE GLYCOSILATED AT RESIDUES N55 AND T57

(75) Inventors: Louise M. Garone, Shrewsbury, MA (US); Stephen J. Arkinstall, Belmont, MA (US); William H. Brondyk, Mansfield, MA (US); Robert K. Campbell, Wrenthan, MA (US); Xuliang Jiang, Braintree, MA (US); Sean D. McKenna, Duxbury, MA (US); Mark Tepper, Newton, MA (US)

(73) Assignee: Merck Serono SA, Coinsins, Vaud (CH)

( * ) Notice: Subject to any disclaimer, the term of this patent is extended or adjusted under 35 U.S.C. 154(b) by 1008 days.

(21) Appl. No.: 10/934,707

(22) Filed: Sep. 2, 2004

(65) Prior Publication Data

US 2005/0100989 A1 May 12, 2005

Related U.S. Application Data

(60) Provisional application No. 60/499,802, filed on Sep. 2, 2003.

(51) Int. Cl.
*A61K 38/24* (2006.01)
*C12N 15/16* (2006.01)
*C07H 21/04* (2006.01)

(52) U.S. Cl. ................... 424/198.1; 435/69.4; 435/325; 435/360; 530/399; 536/23.5

(58) Field of Classification Search ....................... None
See application file for complete search history.

(56) References Cited

U.S. PATENT DOCUMENTS

| 4,589,402 | A | 5/1986 | Hodgen et al. |
| 4,840,896 | A | 6/1989 | Reddy et al. |
| 4,845,077 | A | 7/1989 | Hodgen |
| 4,923,805 | A | 5/1990 | Reddy et al. |
| 5,156,957 | A | 10/1992 | Reddy et al. |
| 5,338,835 | A | 8/1994 | Boime |
| 5,405,945 | A | 4/1995 | Boime et al. |
| 5,508,261 | A | 4/1996 | Moyle et al. |
| 5,639,640 | A | 6/1997 | Reddy et al. |
| 5,767,251 | A | 6/1998 | Reddy et al. |
| 6,653,286 | B1 * | 11/2003 | Mannaerts et al. ............ 514/15 |
| 6,653,338 | B2 | 11/2003 | El Tayer et al. |
| 7,317,095 | B2 | 1/2008 | Brondyk et al. |
| 2002/0127652 | A1 * | 9/2002 | Schambye et al. ......... 435/69.4 |
| 2002/0165159 | A1 | 11/2002 | McCann et al. |
| 2003/0158106 | A1 | 8/2003 | Duerr-Myers et al. |

FOREIGN PATENT DOCUMENTS

EP        521586 A1     1/1993

WO        WO 01/58493 A1   8/2001

OTHER PUBLICATIONS

Bishop, L., et al., "Both of the β-Subunit Carbohydrate Residues of Follicle-Stimulating Hormone Determine the Metabolic Clearance Rate and in Vivo Potency," Endocrinology, vol. 136, pp. 2635-2640 (1995).

Chappel S., et al., "Follicle Stimulating Hormone and Its Receptor: Future Perspectives," Human Reproduction, vol. 13, Supplement 3, pp. 18-35 (1998).

D'Antonio, M., et al., "Biological Characterization of Recombinant Human Follicle Stimulating Hormone Isoforms," Human Reproduction, vol. 14, No. 5, pp. 1160-1167 (1999).

Galway, A., et al., "In Vitro and in Vivo Bioactivity of Recombinant Human Follicle-Stimulating Hormone and Partially Deglycosylated Variants Secreted by Transfected Eukaryotic Cell Lines," Endocrinology, vol. 127, No. 1, pp. 93-100 (1990).

Grossmann, M., "Site-Directed Mutagenesis of Amino Acids 33-44 of the Common ά-Subunit Reveals Different Structural Requirements for Heterodimer Expression Among the Glycoprotein Hormones and Suggests that Cyclic Adenosine 3', 5'-Monophosphate Production and Growth Promotion are Potentially Dissociable Functions of Human Thyrotropin," Molecular Endocrinology, vol. 10, No. 6, pp. 769-779 (1996).

Kelton, C., et al., "The Cloning of the Human Follicle Stimulating Hormone Receptor and Its Expression in COS-7, CHO, and Y-1 Cells," Molecular and Cellular Endocrinology, 89, pp. 141-151 (1992).

Liu, C., et al., "Site-directed Alanine Mutagenesis of Phe$^{33}$, Arg$^{35}$, and Arg$^{42}$-Ser$^{43}$-Lys$^{44}$ in the Human Gonadotropin ά-Subunit," The Journal of Biological Chemistry, vol. 268, No. 29, pp. 21613-21617 (1993).

Roth, K., et al., "Scanning-alanine Mutagenesis of Long Loop Residues 33-53 in Follicle Stimulating hormone Beta Subunit," Molecular and Cellular Endocrinology, vol. 109, pp. 143-149 (1995).

Valove, F., et al., "Receptor Binding and Signal Transduction Are Dissociable Functions Requiring Different Sies on Follicle-Stimulating Hormone," Endocrinology, vol. 135, No. 6, pp. 2657-2661, (1994).

Yoo, J., et al., "COOH-terminal Amino Acids of the ά Subunit Play Common and Different Roles in Human Choriogonadotropin and Follitropin," The Journal of Biological Chemistry, vol. 268, No. 18, pp. 13034-13042 (1993).

Fox, K., et al., "Three-Dimensional Structure of Human Follicle-Stimulating Hormone," Molecular Endocrinology, vol. 15, No. 3, pp. 378-389 (2001).

(Continued)

*Primary Examiner*—Lorraine Spector
(74) *Attorney, Agent, or Firm*—Howrey LLP (57) ABSTRACT

A novel FSH mutant with increased glycosylation and longer half-lifes for use in inducing folliculogenesis in human patients is described. The FSH mutant permits the use of lower cumulative doses of FSH to achieve the same or better clinical result.

12 Claims, 5 Drawing Sheets

OTHER PUBLICATIONS

Klein, J., et al., "Development and Characterization of a Long-Acting Recombinant hFSH Agonist," Human Reproduction, vol. 18, No. 1, pp. 50-56 (2003).

Lapthorn, A., et al., "Crystal Structure of Human Chorionic Gonadotropin," Nature, vol. 369, pp. 455-461 (1994).

Tegoni, M., et al., "Crystal Structure of a Ternary Complex Between Human Chorionic Gonadotropin (hCG) and Two Fv Fragments Specific for the $\alpha$ and $\beta$-Subunits," Journal of Molecular Biology, vol. 289, No. 5, pp. 1375-1385 (1999).

Wu, H., et al., "Structure of Human Chorionic Gonadotropin at 26. A resolution from MAD Analysis of The Selenomethionyl Protein," Structure, vol. 2, No. 6, pp. 545-558 (1994).

* cited by examiner

Note y-axis scale difference between
4x25% and 1 x 100% bar charts

```
                       SEQUENCE LISTING

<160> NUMBER OF SEQ ID NOS: 8

<210> SEQ ID NO 1
<211> LENGTH: 92
<212> TYPE: PRT
<213> ORGANISM: Homo sapiens

<400> SEQUENCE: 1

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys His Cys Ser Thr Cys Tyr Tyr His Lys Ser
                85                  90

<210> SEQ ID NO 2
<211> LENGTH: 111
<212> TYPE: PRT
<213> ORGANISM: Homo sapiens

<400> SEQUENCE: 2

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45
```

```
Lys Thr Cys Thr Phe Lys Glu Leu Val Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 3
<211> LENGTH: 92
<212> TYPE: PRT
<213> ORGANISM: Artificial
<220> FEATURE:
<223> OTHER INFORMATION: alpha subunit mutant H83N

<400> SEQUENCE: 3

Ala Pro Asp Val Gln Asp Cys Pro Glu Cys Thr Leu Gln Glu Asn Pro
1               5                   10                  15

Phe Phe Ser Gln Pro Gly Ala Pro Ile Leu Gln Cys Met Gly Cys Cys
            20                  25                  30

Phe Ser Arg Ala Tyr Pro Thr Pro Leu Arg Ser Lys Lys Thr Met Leu
        35                  40                  45

Val Gln Lys Asn Val Thr Ser Glu Ser Thr Cys Cys Val Ala Lys Ser
    50                  55                  60

Tyr Asn Arg Val Thr Val Met Gly Gly Phe Lys Val Glu Asn His Thr
65                  70                  75                  80

Ala Cys Asn Cys Ser Thr Cys Tyr Tyr His Lys Ser
                85                  90

<210> SEQ ID NO 4
<211> LENGTH: 111
<212> TYPE: PRT
<213> ORGANISM: Artificial
<220> FEATURE:
<223> OTHER INFORMATION: beta subunit mutant E55N/V57T

<400> SEQUENCE: 4

Asn Ser Cys Glu Leu Thr Asn Ile Thr Ile Ala Ile Glu Lys Glu Glu
1               5                   10                  15

Cys Arg Phe Cys Ile Ser Ile Asn Thr Thr Trp Cys Ala Gly Tyr Cys
            20                  25                  30

Tyr Thr Arg Asp Leu Val Tyr Lys Asp Pro Ala Arg Pro Lys Ile Gln
        35                  40                  45

Lys Thr Cys Thr Phe Lys Asn Leu Thr Tyr Glu Thr Val Arg Val Pro
    50                  55                  60

Gly Cys Ala His His Ala Asp Ser Leu Tyr Thr Tyr Pro Val Ala Thr
65                  70                  75                  80

Gln Cys His Cys Gly Lys Cys Asp Ser Asp Ser Thr Asp Cys Thr Val
                85                  90                  95

Arg Gly Leu Gly Pro Ser Tyr Cys Ser Phe Gly Glu Met Lys Glu
            100                 105                 110

<210> SEQ ID NO 5
<211> LENGTH: 26
<212> TYPE: DNA
<213> ORGANISM: Artificial
<220> FEATURE:
<223> OTHER INFORMATION: mutagenesis oligo 1 for alpha H83N
```

```
<400> SEQUENCE: 5
cacacggcgt gcaactgcag tacttg                                        26

<210> SEQ ID NO 6
<211> LENGTH: 26
<212> TYPE: DNA
<213> ORGANISM: Artificial
<220> FEATURE:
<223> OTHER INFORMATION: mutagenesis oligo 2 for alpha H83N

<400> SEQUENCE: 6
caagtactgc agttgcacgc cgtgtg                                        26

<210> SEQ ID NO 7
<211> LENGTH: 49
<212> TYPE: DNA
<213> ORGANISM: Artificial
<220> FEATURE:
<223> OTHER INFORMATION: mutagenesis oligo 1 for beta E55N/V57T

<400> SEQUENCE: 7
gcactctcac tgtttcatat gtcaggttct tgaaggtaca tgttttctg               49

<210> SEQ ID NO 8
<211> LENGTH: 49
<212> TYPE: DNA
<213> ORGANISM: Artificial
<220> FEATURE:
<223> OTHER INFORMATION: mutagenesis oligo 2 for beta E55N/V57T

<400> SEQUENCE: 8
cagaaaacat gtaccttcaa gaacctgaca tatgaaacag tgagagtgc               49
```

FSH BETA MUTANTS THAT ARE GLYCOSILATED AT RESIDUES N55 AND T57

CROSS REFERENCE TO RELATED APPLICATIONS

This application claims the benefit of U.S. Provisional Application Ser. No. 60/499,802, filed Sep. 2, 2003.

BACKGROUND OF THE INVENTION

1. Field of the Invention

The present invention relates to polypeptides exhibiting follicle stimulating hormone activity, to methods for preparing such polypeptides, and to the use of such polypeptides in therapy, in particular in the treatment of reproductive disorders.

2. Description of Related Art a. Gonadotropins

Follicle stimulating hormone (FSH) is a member of the family of gonadotrophins that play key roles in human fertility. The gonadotrophins, which also include luteinising hormone (LH) and chorionic gonadotrophin (CG), are heterodimers, each consisting of a common α-subunit (92 amino acids) and a unique β-subunit (111 amino acids in FSH). The amino acid sequences of the mature forms of the α- and β-subunits are shown in SEQ ID NO. 1 and SEQ ID NO. 2, respectively.

Human FSH has been isolated from pituitary glands and from postmenopausal urine (EP 322,438) and has been produced recombinantly in mammalian cells (U.S. Pat. No. 5,639,640, U.S. Pat. No. 5,156,957, U.S. Pat. No. 4,923,805, U.S. Pat. No. 4,840,896, U.S. Pat. No. 5,767,251, EP 211,894 and EP 521,586). The latter references also disclose the human FSH β-subunit gene. U.S. Pat. No. 5,405,945 discloses a modified human α-subunit gene comprising only one intron.

Liu et al., J Biol Chem 1993, 15; 268 (2): 21613-7, Grossmann et al., Mol Endocrinol 1996 10 (6): 769-79, Roth and Dias (Mol Cell Endocrinol 1995 1; 109 (2): 143-9, Valove et al., Endocrinology 1994; 135 (6): 2657-61, Yoo et al., J Biol Chem 1993 25; 268 (18): 13034-42), U.S. Pat. No. 5,508,261 and Chappel et al., 1998, Human Reproduction, 13 (3): 1835 disclose various structure-function relationship studies and identify amino acid residues involved in receptor binding and activation and in dimerization of FSH.

b. Use of Gonadotropins in Assisted Reproductive Techniques

The gonadotrophins play crucial roles in the reproductive cycle, and their use in exogenous therapies is essential for assisted reproductive techniques (ART), such as in vitro fertilization (IVF), IVF in conjunction with intracytoplasmic sperm injection (IVF/ICSI) and embryo transfer (ET), as well as for ovulation induction (OI) in anovulatory patients undergoing in vivo fertilization either naturally or through intrauterine insemination (IUI).

U.S. Pat. No. 4,589,402 and U.S. Pat. No. 4,845,077 disclose purified human FSH which is free of LH and the use thereof for in vitro fertilization. EP 322 438 discloses a protein with at least 6200 U/mg FSH activity which is substantially free of LH activity, and wherein the FSH α-subunit and the β-subunit, respectively, may be wild type or specified truncated forms thereof.

Prolonged therapy is necessary to achieve a therapeutic effect, typically for 8-10 consecutive days and sometimes up to 21 days to stimulate folliculogenesis in women, and for up to 18 months in hypogonadotrophic males to induce spermatogenesis. Recombinant hFSH is typically administered as an i.m. or s.c. daily injection, with consequent discomfort and potential for local injection site reaction. Decreasing the frequency of administration would facilitate therapy and render gonadotrophin administration more convenient, more tolerable and patient-friendly.

c. Glycosylation of FSH

The gonadotrophins are glycoproteins, with each sub-unit having asparagine-linked (N-linked) oligosaccharide side chains that are important for in vivo activity and function. Carbohydrate addition (glycosylation) to polypeptides is a post-translational event that results in the addition of sugar chains to specific asparagine (N-linked) or serine/threonine (O-linked) amino acids. In contrast to the invariant amino acid sequence of the protein portion of glycoproteins, the carbohydrate structures are variable, a feature referred to as microheterogeneity. For example, N-glycosylation sites on the same protein may contain different carbohydrate structures. Furthermore, even at the same glycosylation site on a given glycoprotein, different carbohydrate structures may be found. This heterogeneity is a consequence of the non-template-directed synthesis of carbohydrates.

N-glycosylation of proteins occurs specifically at the consensus pattern Asn-Xaa-Ser/Thr, and to a lesser extent at the consensus pattern Asn-Xaa-Cys, where Xaa can be any amino acid residue. However, the presence of a consensus tripeptide is not sufficient to insure that an asparagine residue will be glycosylated. For example, N-glycosylation of the Asn-Pro-Ser/Thr sequence occurs at a rate 50-times lower than the other consensus patterns of Asn-Xaa-Ser/Thr.

Human FSH contains four N-linked glycosylation sites: two on the common α-subunit at positions 52 and 78 and two on the β-subunit at positions 7 and 24. Carbohydrates attached to the α-subunit of FSH are critical for dimer assembly, integrity, secretion and signal transduction, whereas β-subunit carbohydrates are important for dimer assembly, secretion and clearance of the heterodimer from the circulation.

Galway et al., Endocrinology 1990; 127 (1): 93-100 demonstrate that FSH variants produced in a N-acetylglucosamine transferase-I CHO cell line or a CHO cell line defective in sialic acid transport are as active as FSH secreted by wild type cells or purified pituitary FSH in vitro, but lacked in vivo activity, presumably due to rapid clearance of the inadequately glycosylated variants in serum. D'Antonio et al., Human Reprod 1999; 14 (5): 1160-7 describe various FSH isoforms circulating in the blood stream. The isoforms have identical amino acid sequences, but differ in their extent of post-translational modification. It was found that the less acidic isoform group had a faster in vivo clearance as compared with the acidic isoform group, possibly due to differences in the sialic acid content between the isoforms. Moreover, Bishop et al. Endocrinology 1995; 136 (6): 2635-40 conclude that circulatory half-life appears to be the primary determinant of in vivo activity. These observations led to the hypothesis that the half-life of FSH could be increased by introducing additional glycosylation sites to increase the sialic acid content of the polypeptide.

d. FSH Variants

FSH agonists with increased half-lives have been developed by fusing the carboxyterminal peptide of hCG (CTP) to native recombinant human FSH (rhFSH). The CTP moiety consists of amino acids 112-118 to 145 with four O-linked glycosylation sites located at positions 121, 127, 132 and 138. U.S. Pat. No. 5,338,835 and U.S. Pat. No. 5,585,345 disclose a modified FSH β-subunit extended at the C-terminal Glu with the CTP moiety of hCG. The resulting modified analogue is stated to have the biological activity of native FSH, but a prolonged circulating half-life. U.S. Pat. No. 5,405,945 discloses that the carboxy terminal portion of the hCG β-subunit or a variant thereof has significant effects on the clearance of CG, FSH, and LH.

U.S. Pat. No. 5,883,073 discloses single-chain proteins comprised of two α-subunits with agonist or antagonist activity for CG, TSH, LH and FSH. U.S. Pat. No. 5,508,261 discloses heterodimeric polypeptides having binding affinity to LH and FSH receptors comprising a glycoprotein hormone α-subunit and a non-naturally occurring β-subunit polypeptide, wherein the β-subunit polypeptide is a chain of amino acids comprising four joined subsequences, each of which is selected from a list of specific sequences. Klein et al. (2003) discloses a single chain analogue of FSH with an increased half-life, wherein the α- and β-subunits are linked by an oligopeptide containing two N-linked glycosylation sites.

WO 01/58493 discloses 77 mutations that may be made in the α-subunit of FSH and 51 mutations that may be made in the β-subunit of FSH in an attempt to improve the in vivo half-life of FSH. WO 01/58493 discloses that the mutant α- and β-subunits may be used individually (1 additional glycosylation site) or in combination (2 additional glycosylation sites). The 128 candidate mutants were identified by using 50 models of the 3D structure of FSH that were generated based solely on the structure of hCG and a sequence alignment of FSH and hCG despite only 32% identity between the β-subunits of hCG and FSH. WO 01/58493 does not disclose the production or testing of any α- or β-subunits of FSH where a glycosylation site was introduced by site directed mutagenesis.

A clinical need exists for a product which provides part or all of the therapeutically relevant effects of FSH, and which may be administered at less frequent intervals as compared to currently available FSH products, and which preferably provides a more stable level of circulating FSH activity as compared to that obtainable by current treatment.

The present invention is directed to such products as well as the means of making such products.

SUMMARY OF THE INVENTION

The present invention relates to a mutant FSH, wherein the FSH α-subunit comprises the sequence of SEQ ID NO. 3, and wherein the FSH β-subunit comprises the sequence of SEQ ID NO:4. The mutant FSH may be N-glycosylated at 0, 1, 2, 3, 4, 5 or 6 asparagine residues of said mutant FSH. N83 of the mutant α-subunit may be glycosylated. N55 of the mutant β-subunit may be glycosylated. T57 of the mutant β-subunit may also be glycosylated.

The present invention also relates to an isolated DNA encoding an FSH α-subunit mutant comprising the sequence of SEQ ID NO. 3. The present invention also relates to an isolated DNA encoding an FSH β-subunit mutant comprising the sequence of SEQ ID NO. 4.

The present invention also relates to a vector comprising DNA encoding an FSH α-subunit mutant comprising the sequence of SEQ ID NO. 3. The vector may be an expression vector.

The present invention also relates to a vector comprising DNA encoding an FSH β-subunit mutant comprising the sequence of SEQ ID NO. 4. The vector may be an expression vector.

The present invention also relates to a vector comprising a first DNA and a second DNA, wherein the first DNA encodes an FSH α-subunit mutant comprising the sequence of SEQ ID NO. 3 and the wherein second DNA encodes an FSH β-subunit mutant comprising the sequence of SEQ ID NO. 4. The vector may be an expression vector.

The present invention also relates to a cell comprising a vector comprising DNA encoding an FSH α-subunit mutant comprising the sequence of SEQ ID NO. 3. The vector may be an expression vector. The cell may be a mammalian cell.

The present invention also relates to a cell comprising a vector comprising DNA encoding an FSH β-subunit mutant comprising the sequence of SEQ ID NO. 4. The vector may be an expression vector. The cell may be a mammalian cell.

The present invention also relates to a cell comprising a vector comprising a first DNA and a second DNA, wherein the first DNA encodes an FSH α-subunit mutant comprising the sequence of SEQ ID NO. 3 and wherein the second DNA encodes an FSH β-subunit mutant comprising the sequence of SEQ ID NO. 4. The vector may be an expression vector. The cell may be a mammalian cell.

The present invention also relates to a cell comprising a first and a second vector, wherein the first vector comprises DNA encoding an FSH α-subunit mutant comprising the sequence of SEQ ID NO. 3 and wherein the second vector comprises DNA encoding an FSH β-subunit mutant comprising the sequence of SEQ ID NO. 4. The vector may be an expression vector. The cell may be a mammalian cell.

The present invention also relates to a method for producing an FSH mutant comprising culturing mammalian cells capable of glycosylating proteins, wherein said cells comprise a first expression vector comprising DNA encoding an FSH α-subunit comprising the sequence of SEQ ID NO. 3 and a second expression vector comprising DNA encoding an FSH β-subunit comprising the sequence of SEQ ID NO. 4.

The present invention also relates to a composition comprising an FSH mutant and a pharmaceutically acceptable carrier or excipient, wherein the FSH α-subunit comprises the sequence of SEQ ID NO. 3, and wherein the FSH β-subunit comprises the sequence of SEQ ID NO. 4.

The present invention also relates to a method of treating an infertile mammal, comprising administering to a mammal in need thereof an effective amount of a mutant FSH mutant, wherein the FSH α-subunit comprises the sequence of SEQ ID NO. 3, and wherein the FSH β-subunit comprises the sequence of SEQ ID NO. 4.

The present invention also relates to a method of stimulating folliculogenesis in a mammal, comprising administering to a mammal in need thereof an effective amount of a mutant FSH mutant, wherein the FSH α-subunit comprises the sequence of SEQ ID NO. 3, and wherein the FSH β-subunit comprises the sequence of SEQ ID NO. 4.

The present invention also relates to a method of inducing ovarian hyperstimulation in a mammal, comprising administering to a mammal in need thereof an effective amount of a mutant FSH mutant, wherein the FSH α-subunit comprises the sequence of SEQ ID NO. 3, and wherein the FSH β-subunit comprises the sequence of SEQ ID NO. 4.

DETAILED DESCRIPTION OF THE INVENTION

While it has been shown that increasing the carbohydrate content of FSH may lead to increased in vivo half-life, improving the half-life of FSH is more complicated than simply adding additional glycosylation sites. While a glycosylation consensus sequence is necessary for carbohydrate addition, it is not sufficient to ensure that a carbohydrate addition site will be utilized. Other factors, such as the local protein folding and conformation during biosynthesis, determine whether an oligosaccharide is attached at a given consensus sequence site. In addition, the consensus sequence must be in a position such that glycosylation of the site does not interfere with receptor binding, or compromise the folding, conformation or stability of the glycoprotein.

To this point, FSH analogues with increased half-lives have been limited to fusion proteins wherein the fused portion of the polypeptide included additional glycosylation sites. FSH analogues with increased half-lives have yet to be produced by the introduction of glycosylsation sites by site directed mutagenesis.

Structural knowledge of FSH is critical when adding glycosylation sites by site directed mutagenesis because the consensus residues need to be added at positions that are compatible with carbohydrate addition. If a glycosylation site is introduced by mutation, the mutated residues should not disrupt the three-dimensional structure of the protein or substantially detract from the desired function of the protein, such as receptor binding or activation. Furthermore, the consensus residues should not be added such that they are buried in the interior of the folded protein structure, otherwise it is unlikely that glycosylation will occur at the particular site.

Until recently, the three-dimensional structure of gonadotrophins was limited to two independent reports of the crystal structure of hCG: one structure of partially deglycosylated hCG (Lapthorn et al., 1994; Wu et al., 1994) and a low resolution structure of the ternary complex of fully glycosylated hCG and two Fv fragments (Tegoni et al., 1999).

Although hCG and FSH have essentially identical folding patterns, the two structures are significantly different (Fox et al, 2001), and the detailed structure for individual amino acid residues for the FSH molecule cannot be properly modeled from the previously determined hCG structures (Wu et al, 1994; Lapthorn et al, 1994).

The present invention is directed to an FSH mutant that was designed solely on the 3D crystal structure of the human FSH molecule (Fox et al, 2001). The FSH mutant of the present invention ("GM-1") has been modified to introduce the following substitutions to create additional glycosylation recognition sites: H83N of the α-subunit and E55N/V57T of the β-subunit. One or more of the additional glycosylation sites of the recombinant FSH may be glycosylated. The one or more additional glycosylation sites of the mutant FSH may be glycosylated in vitro or in vivo.

The FSH mutant of the present invention may be produced by any suitable method known in the art. These methods include the construction of nucleotide sequences encoding the respective FSH mutants and expressing the amino acid sequence in a suitable transfected host. The FSH mutant of the present invention may also be produced by chemical synthesis or by a combination of chemical synthesis and recombinant DNA technology.

The FSH mutant of the present invention may comprise the α- and β-subunits of FSH in the form of two separate polypeptide chains, where the two chains become dimerized in vivo so as to form a dimeric polypeptide, or it may comprise a single chain construct comprising the two subunits covalently linked by a peptide bond or a peptide linker. The amino acid residues of the linker peptide may exhibit properties that do not interfere significantly with the activity of the FSH mutant.

The FSH mutant of the present invention may have an increased half-life compared to wild type FSH. The FSH mutant of the present invention may also have increased stability compared to wild type FSH. The FSH mutant may comprise oligosaccharides at 0, 1, 2, 3, 4, 5 or 6 of the N-linked glycosylation sites. The FSH-mutant may comprise one or more FSH mutant isoforms, wherein each isoform comprises oligosaccharides at 0, 1, 2, 3, 4, 5 or 6 of the N-linked glycosylation sites.

The nucleotide sequence encoding the α- or β-subunits of the FSH mutants of the invention may be constructed by isolating or synthesizing a nucleotide sequence encoding the parent FSH subunit, such as the hFSH-alpha or hFSH-beta with the amino acid sequences shown in SEQ ID NOS: 3 and 4, respectively. The nucleotide sequence may then be changed so as to effect the substitution of the relevant amino acid residues. The nucleotide sequence can be modified by site directed mutagenesis. In the alternative, the nucleotide sequence may be prepared by chemical synthesis, wherein oligonucleotides are designed based on the specific amino acid sequence of the FSH mutant.

The nucleotide sequence encoding the polypeptide may be inserted into a recombinant vector and operably linked to control sequences necessary for expression of the polypeptide in the desired transfected host cell. One of skill in the art may make a selection among these vectors, expression control sequences and hosts without undue experimentation. The recombinant vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

The vector may be an expression vector in which the nucleotide sequence encoding the polypeptide of the invention is operably linked to additional segments required for transcription of the nucleotide sequence. The vector may be derived from plasmid or viral DNA. A number of suitable expression vectors for expression in the host cells mentioned herein are commercially available or described in the literature.

The recombinant vector may further comprise a DNA sequence enabling the vector to replicate in the host cell in question. An example of such a sequence, (when the host cell is a mammalian cell) is the SV40 origin of replication. The vector may also comprise a selectable marker, e.g. a gene whose product complements a defect in the host cell, such as the gene coding for dihydrofolate reductase (DHFR) or one which confers resistance to a drug, e.g. ampicillin, kanamycin, tetracycline chloramphenicol, neomycin, hygromycin or methotrexate.

The vector may also comprise an amplifiable gene, such as DHFR, such that cells having multiple copies of the amplifiable gene and flanking sequences, including the mutant FSH DNA, can be selected for on appropriate media. The term "control sequences" is defined herein to include all components which are necessary or advantageous for the expression of the polypeptide of the invention. Examples of suitable control sequences for directing transcription in mammalian cells include the early and late promoters of SV40 and adenovirus, e.g. the adenovirus 2 major late promoter, the MT-1 (metallothionein gene) promoter and the human cytomegalovirus immediate-early gene promoter (CMV).

The present invention is also related to isolated DNA encoding an H83N α-subunit and an isolated DNA encoding an E55N/V57T β-subunit of FSH. The nucleotide sequences of the invention encoding the FSH mutants, whether prepared by site-directed mutagenesis, synthesis, PCR or other methods, may optionally also include a nucleotide sequence that encodes a signal peptide. The signal peptide is present when the polypeptide is to be secreted from the cells in which it is expressed. Such signal peptide, if present, should be one recognized by the cell chosen for expression of the polypeptide. The signal peptide may be homologous (e.g. be that normally associated with a hFSH subunit) or heterologous (i.e. originating from another source than hFSH) to the polypeptide or may be homologous or heterologous to the host cell, i.e. be a signal peptide normally expressed from the host cell or one which is not normally expressed from the host cell.

Any suitable host may be used to produce the polypeptide subunits of the invention, including bacteria, fungi (including yeasts), plant, insect, mammal, or other appropriate animal cells or cell lines, as well as transgenic animals or plants. Examples of suitable mammalian host cells include Chinese hamster ovary (CHO) cell lines, (e.g. CHO-KL; ATCC CCL-61), Green Monkey cell lines (COS) (e.g. COS 1 (ATCC CRL-1650), COS 7 (ATCC CRL-1651)); mouse cells (e.g. NSIO), Baby Hamster Kidney (BI-EK) cell lines (e.g. ATCC CRL-1632 or ATCC CCL-10), and human cells (e.g. BEK 293 (ATCC CRL-1573)), as well as plant cells in tissue culture. Additional suitable cell lines are known in the art and available from public depositories such as the American Type Culture Collection, USA. Methods for introducing exogeneous DNA into mammalian host cells include calcium phosphate-mediated transfection, electroporation, DEAE-dextran mediated transfection, liposome-mediated transfection and viral vectors.

Cells may be cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermenters performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g. in catalogues of the American Type Culture Collection). If the polypeptide is secreted into the nutrient medium, it can be recovered directly from the medium. If the polypeptide is not secreted, it can be recovered from cell lysates.

The resulting mutant FSH polypeptide may be recovered by methods known in the art. For example, it may be recovered from the nutrient medium by conventional procedures including, but not limited to, centrifugation, filtration, extraction, spray drying, evaporation, or precipitation. The mutant FSH polypeptides may be purified by a variety of procedures known in the art including, but not limited to, chromatography (e.g. ion exchange, affinity, hydrophobic, chromatofocusing, and size exclusion), electrophoretic procedures (e.g. preparative isoelectric focusing), differential solubility (e.g. ammonium sulfate precipitation), SDS-PAGE, or extraction.

The present invention is also related to a pharmaceutical composition comprising the FSH mutant according to the invention. Such pharmaceutical compositions can be used to stimulate folliculogenesis, for example in conjunction with ovulation induction or assisted reproductive techniques (ART). Because the FSH mutant of the present invention is particularly effective in inducing multiple follicles to develop and mature, it is particularly suitable for use in ART, in which it is desired to collect multiple oocytes.

Alternatively, with careful tailoring of the dose, the FSH mutant of the invention may be used to induce mono-folliculogenesis for OI, or paucifolliculogenesis (up to about three follicles) for IUI, for in vivo fertilization. Mono-folliculogenesis can also be attained with a reduced dose of the FSH mutant, or less frequent dosing as compared with conventional FSH preparations. For example, in OI an FSH preparation of the invention may be administered at 225-400 IU every three days, or lower doses, depending on the patient response. Patient response may be followed by sonography.

The FSH mutant of the invention may be used in a controlled ovarian hyperstimulation (COH) regimen. Standard regimens for COH include a down-regulation phase in which endogenous luteinising hormone (LH) is down-regulated by administration of a gonadotrophin releasing hormone (GnRH) agonist followed by a stimulatory phase in which follicular development (folliculogenesis) is induced by daily administration of follicle stimulating hormone (FSH), usually at about 150-225 IU/day. Alternatively stimulation is started with FSH after spontaneous or induced menstruation, followed by administration of a GnRH-antagonist (typically starting around day six of the stimulatory phase). When there are at least 3 follicles>16 mm (one of 18 mm), a single bolus of hCG (5-10,000 IU) is given to mimic the natural LH surge and induce ovulation. Oocyte recovery is timed for 36-38 hours after the hCG injection.

The FSH mutant of the invention may also be used for OI and IUI. For example, FSH stimulation with a preparation of the invention is started after spontaneous or induced menstruation, at a daily dose of 75-150 IU. When 1 or 3 follicles have reached a diameter of at least 16 mm, a single bolus of hCG is administered to induce ovulation. Insemination is performed in vivo, by regular intercourse or IUI.

Because the FSH mutant of the present invention may have an increased half-life with respect to wild type FSH preparations, regimens such as that described above may employ lower IU doses of FSH, and/or may be modified by decreasing the FSH stimulation period, while achieving the same or better response, in terms of number and viability of follicles. For example, using an FSH preparation of the invention, adequate folliculogenesis may be achieved with daily doses of at or about 50-150 IU FSH, preferably at or about 50-100, more preferably at or about 50-75 IU FSH. Dosing of FSH is usually on a daily or semi-daily basis. The dosing period may be less than at or about 14 days, preferably less than at or about 12 days, more preferable less than at or about 11 or 10 days. For OI, the FSH mutant preparations of the invention may be administered at doses from 25-150 IU FSH/day, preferably, 50-125 IU FSH/day. For the treatment of male infertility, an FSH mutant preparation of the invention may be administered at 3×150 to 300 IU/week until spermatogenesis reaches levels adequate for insemination, either through regular intercourse or ART techniques.

Because of the longer half-life of the mutant FSH of the present invention, it may be administered as a long-acting preparation. Conventional FSH may be administered at or about 300 IU on every second day, while achieving similar results to administration every day at or about 150 IU. The expression "long-acting" is meant to encompass FSH preparations that may be administered less frequently than every two days. The mutant FSH of the present invention may be administered every three days, every four days, every five days, every six days or every seven days, while achieving similar or better results than daily administration of conventional FSH.

In a related aspect, the FSH mutant or pharmaceutical compositions comprising the FSH mutant are used for the manufacture of a medicament for treatment of diseases, disorders or conditions. In another aspect, the polypeptide or the pharmaceutical composition according to the invention is used in a method of treating a mammal, in particular a human, comprising administering to the mammal in need thereof such polypeptide or pharmaceutical composition.

It will be apparent to those of skill in the art that an effective amount of a polypeptide, preparation or composition of the invention depends, inter alia, upon the disease, the dose, the administration schedule, whether the polypeptide or preparation or composition is administered alone or in conjunction with other therapeutic agents, the serum half-life of the compositions, and the general health of the patient. Typically, an effective dose of the preparation or composition of the invention is sufficient to ensure a therapeutic effect.

The FSH mutant of the present invention may be administered in a composition including one or more pharmaceutically acceptable carriers or excipients. "Pharmaceutically acceptable" means a carrier or excipient that does not cause any untoward effects in patients to whom it is administered. Such pharmaceutically acceptable carriers and excipients are well known in the art, and the polypeptide of the invention can be formulated into pharmaceutical compositions by well-known methods (see e.g. Remington's Pharmaceutical Sciences, 18th edition, A. R. Gennaro, Ed., Mack Publishing Company (1990); Pharmaceutical Formulation Development of Peptides and Proteins, S. Frokjaer and L. Hovgaard, Eds., Taylor & Francis (2000); and Handbook of Pharmaceutical Excipients, 3rd edition, A. Kibbe, Ed., Pharmaceutical Press (2000)). Pharmaceutically acceptable excipients that may be used in compositions comprising the polypeptide of the invention include, for example, buffering agents, stabilizing agents, preservatives, isotonifiers, nonionic surfactants or detergents "wetting agents"), antioxidants, bulking agents or fillers, chelating agents and cosolvents.

The pharmaceutical composition of the invention comprising the FSH mutant may be formulated in a variety of forms, including liquids, e.g. ready-to-use solutions or suspensions, gels, lyophilized, or any other suitable form, e.g. powder or crystals suitable for preparing a solution. The form of the composition may depend upon the particular indication being treated and will be apparent to one of skill in the art.

The pharmaceutical composition comprising the FSH mutant of the invention may be administered intravenously, intramuscularly, intraperitoneally, intradermally, subcutaneously, sublingualy, buccally, intranasally, transdermally, by inhalation, or in any other acceptable manner, e.g. using PowderJect or ProLease technology or a pen injection system. The mode of administration may depend upon the particular indication being treated and will be apparent to one of skill in the art. The composition may be administered subcutaneously, since this may allow the patient to conduct self-administration.

The pharmaceutical compositions of the invention may be administered in conjunction with other therapeutic agents. These agents may be incorporated as part of the same pharmaceutical composition or may be administered separately from the polypeptide of the invention, either concurrently or in accordance with any other acceptable treatment schedule. In addition, the polypeptide, preparation or pharmaceutical composition of the invention may be used as an adjunct to other therapies.

The present invention has multiple aspects, illustrated by the following non-limiting examples.

Example 1

Single FSH Mutants

Identification of Candidate Glycosylation Sites

The 3D crystal structure of human FSH was used to identify candidate glycosylation sites in the α- and β-subunits of FSH. Two FSH molecules (four subunits) are present in each asymmetric unit of the crystal structure. The two FSH molecules were superimposed and compared, with each residue being visually inspected to identify potential N-glycosylation sites. The crystallographic structure of FSH was combined with the knowledge of the FSH/FSHR receptor interaction to further aid in the selection of potential N-glycosylation sites. The principal design criteria were minimal disruption of 3D structure, minimal disruption of predicted binding and activation sites, and predictable 3D structure compatible with glycosylation.

Based on the above criteria, twenty single mutants (8α and 12β) were made to the amino acid sequence of FSH including the following two mutants:

| | |
|---|---|
| α-subunit | H83N |
| β-subunit | E55N/V57T |

Transient Expression of Single FSH Mutants

Each of the mutants was obtained by performing site directed mutagenesis in a manner similar to that described in Example 3. The mutants were transiently expressed on a small scale in CHO-Dukx cells together with the complementary wild type subunit in a manner similar to that described in Example 4. ELISA analysis of the resulting culture supernatants indicated that 19 of the 20 mutants were able to be transiently expressed. The range of levels for transient expression of controls and mutants was 0-1.95 μg/ml with the mean 0.59 and median 0.5 μg/ml, respectively, and 0 μg/ml repeatedly confirmed in mock transfections.

Morphological Analysis of Single FSH Mutants

Aliquots of concentrated culture supernatants from transient expression of the single FSH mutants were analyzed electrophoretically under non-reduced LDS PAGE conditions that permitted the resolution of intact FSH heterodimers from free α- and β-subunits. Proteins were electrophoretically transferred to PVDF and analyzed using primary antibodies directed against the α- and β-subunits of FSH. A number of different vendors' primary antibodies were tested in pre-screening and occasionally used thereafter as confirmation analyses but the most uniformly useful primary antibodies proved to be Chromaprobe BHS 104 (biotinylated polyclonal goat anti FSH α-subunit) at 1.5 μg/ml and Chromaprobe BHS 105 (murine monoclonal anti FSH β-subunit) at 1.5 μg/ml.

Two additional types of morphological analysis complemented the Western blots of heterodimer-intact samples. Western analysis of heterodimer-dissociated samples and autoradiography of electrophoretically separated heterodimer-dissociated immune precipitates of mutants and controls metabolically labeled with $^{35}$S-Cys.

Of the 19 expressible FSH mutants, only five mutants showed increased glycosylation as evidenced by a shift of the distribution of the apparent molecular weight of the subunit or heterodimer. The five mutants showing increased glycosylation included one α-subunit mutant and four β-subunit mutants, including β E55N/V57T.

Interestingly, the α-subunit mutant αH83N did not show evidence of increased glycosylation but did appear to lead to an increased abundance of heterodimer in the protein population relative to the heterodimer abundance among wild-type FSH subunits coexpressed under the same transient conditions.

Half-Life of Transiently Expressed Single FSH Mutants

The pharmacokinetics of the five hyperglycosylated single mutants obtained by transient expression, including β E55N/V57T, were compared to Gonal-F. Gonal-F is a recombinant form of FSH that is indistinguishable from native hFSH. The FSH content of the injection material and of rat serum samples collected at preset times following injection for each PK experiment were quantified by ELISA. None of the 5 single mutants, including the β-subunit mutant E55N/V57T, demonstrated a half-life greater than that of the control Gonal-F.

Purification and Analysis of Single Site Glycosylation Mutants

Three of the four hyperglycosylated single β-subunit mutants, including the E55N/V57T mutant, were expressed and purified by immunoaffinity chromatography. The in vitro activity of the three hyperglycosylated β-subunit mutants, including the E55N/V57T mutant, was compared to recombinant FSH by looking at (i) the ability to compete with $^{125}$I radiolabelled FSH for binding to a membrane preparations containing the human FSH receptor ($K_i$) and the ability to stimulate FSHR-coupled cAMP production ($EC_{50}$):

|  | $K_i$ | $EC_{50}$ |
|---|---|---|
| β E55N/V57T | $8.6 \times 10^{-10}$ M | $3.9 \times 10^{-11}$ M |
| rhFSH | $4.8 \times 10^{-10}$ M | $1.2 \times 10^{-11}$ M |

The results above show that the β-subunit mutant E55N/V57T has in vitro activity comparable to that of wild type FSH. In fact, each of the three single β-subunit mutants have in vitro activity comparable to that of wild type FSH. Moreover, mass spectrometry analysis of the purified single β-subunit mutants indicated that mass distribution shifts were seen with each of the three mutants. However, no single glycosylation mutant demonstrated a substantially-prolonged half life when the pharmacokinetics of the purified proteins were determined following a single iv injection of immature female rats. Compared to rhFSH which has a half-life of 3.8±0.6 h, β E55N/V57T has a half-life of 4.8±0.4.

Example 2

Production and Analysis of Double Glycosylation Mutants

Due to the failure of the single α- and β-subunit single mutants to improve the half-life of FSH, two of the single α-subunit mutants were combined with three of the single β-subunit in a transient expression to create six different double mutants including GM-1, which comprises the α-subunit mutant H83N and the β-subunit mutant E55N/V57T.

Five of the six double mutants, including GM-1, were able to be expressed. The expressible five double mutants were analyzed for the ability to stimulate FSHR-coupled cAMP production. Each of the five double mutants, including GM-1, were comparable to rhFSH in the ability to stimulate FSHR-coupled cAMP production in vivo.

The pharmacokinetics of the same five double mutants of FSH were also compared to recombinant hFSH and CTP-FSH. The results in Table 1 indicate that GM-1 has a half-life significantly higher than rhFSH and approaching that of CTP-FSH.

TABLE 1

| Pharmacokinetics | |
|---|---|
| Protein | $t_{1/2}$ (h) |
| rhFSH | 3.4 ± 0.5 |
| CTP-FSH | 7.6 ± 2.6 |
| GM-1 | 5.1 ± 1.6 |

The increased half-life of GM-1 is surprising considering that the single β-subunit mutant E55N/V57T by itself had no effect on half life. Additionally surprising is the increased half-life of GM-1 considering that the α-subunit mutant H83N did not lead to increased glycosylation.

Example 3

Production of GM-1

The cDNAs of the α- and β-subunits of human FSH were subcloned into the pDONR vector (Invitrogen). The QuikChange™ Site-Directed Mutagenesis Kit (Stratagene) was used to introduce the N-linked glycosylation sites into the α- and β-subunits of FSH. The QuikChange™ system utilizes two synthetic oligonucleotide primers containing the desired mutation(s). The following pairs of oligonucleotides were used to introduce the N-linked glycosylation sites:

TABLE 2

| Oligonucleotides | | | |
|---|---|---|---|
| Subunit | Mutation | Oligo | SEQ ID NO. |
| α | H83N | cacacggcgtgcaactgcagtacttg | SEQ ID NO. 5 |
| α | H83N | caagtactgcagttgcacgccgtgtg | SEQ ID NO. 6 |
| β | E55N, V57T | gcactctcactgtttcatatgtcaggttcttgaaggtacatgttttctg | SEQ ID NO. 7 |
| β | E55N, V57T | cagaaaacatgtaccttcaagaacctgacatatgaaacagtgagagtgc | SEQ ID NO. 8 |

The sequence of the mutants was confirmed by using the ABI PRISM BigDye™ Terminator v3.0 Ready Reaction Cycle Sequencing Kit followed by analysis with the ABI PRISM 310 Genetic Analyzer.

Figure 1:
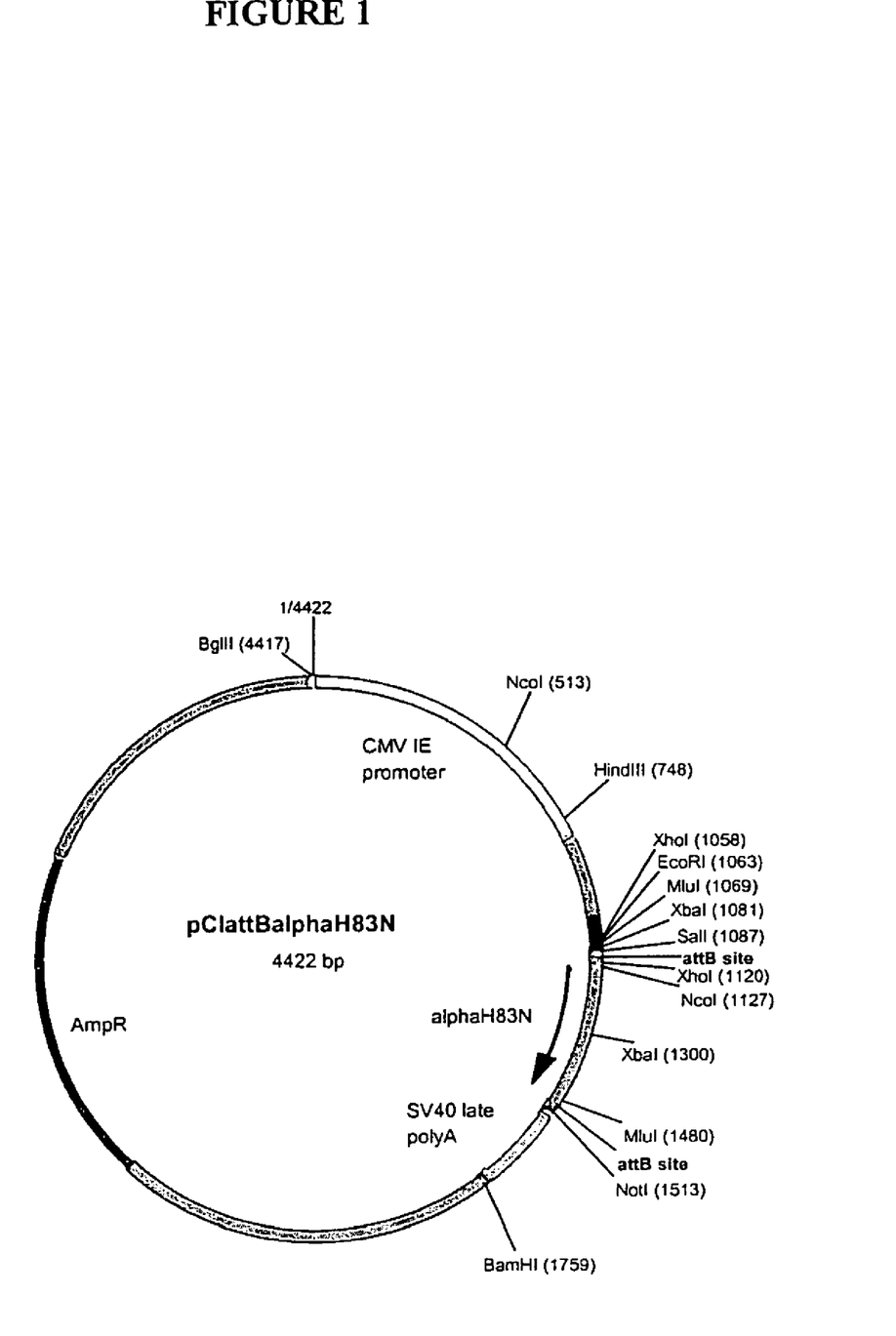
FIG. 1 shows the plasmid map of the expression vector used for the expression of the αH83N subunit.
Figure 2:
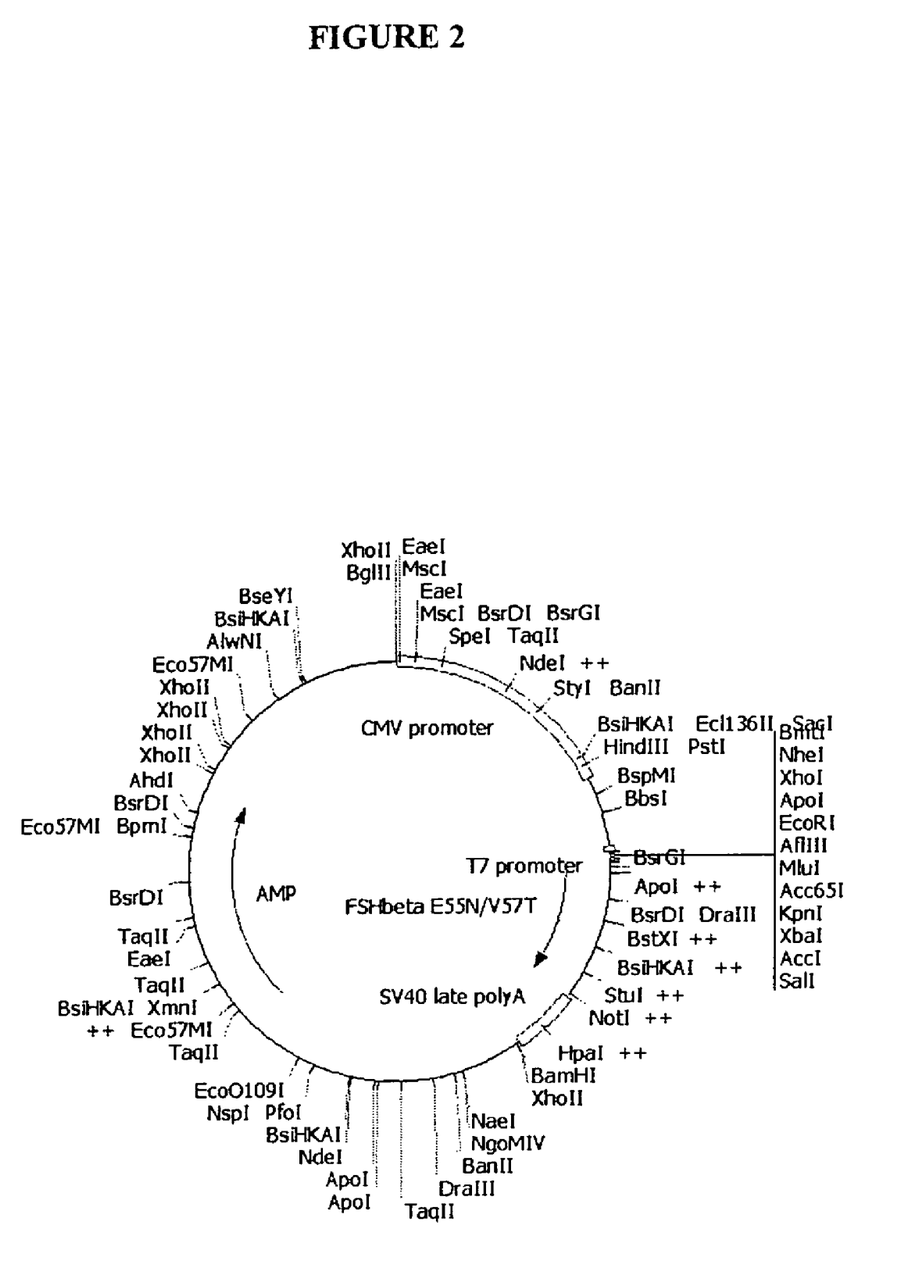
FIG. 2 shows the plasmid map of the expression vector used for the transient expression of the βE55/V57T subunit.

The αH83N and βE55/V57T mutants were subcloned into a modified pCI expression vector using the Gateway™ Cloning Technology (Invitrogen) to yield plasmids p13251 and p13252, as shown in FIGS. 1 and 2. The pCI mammalian expression vector (Promega) had previously been converted into a GATEWAY destination vector by using the GATEWAY Vector Conversion System (Invitrogen). The pCI expression vector contains the human cytomegalovirus immediate-early enhancer/promoter to regulate the expression of the inserted gene, an intron upstream of the gene to promote expression and the simian virus 40 late polyadenylation signal downstream from the inserted gene to terminate transcription.

Figure 3:
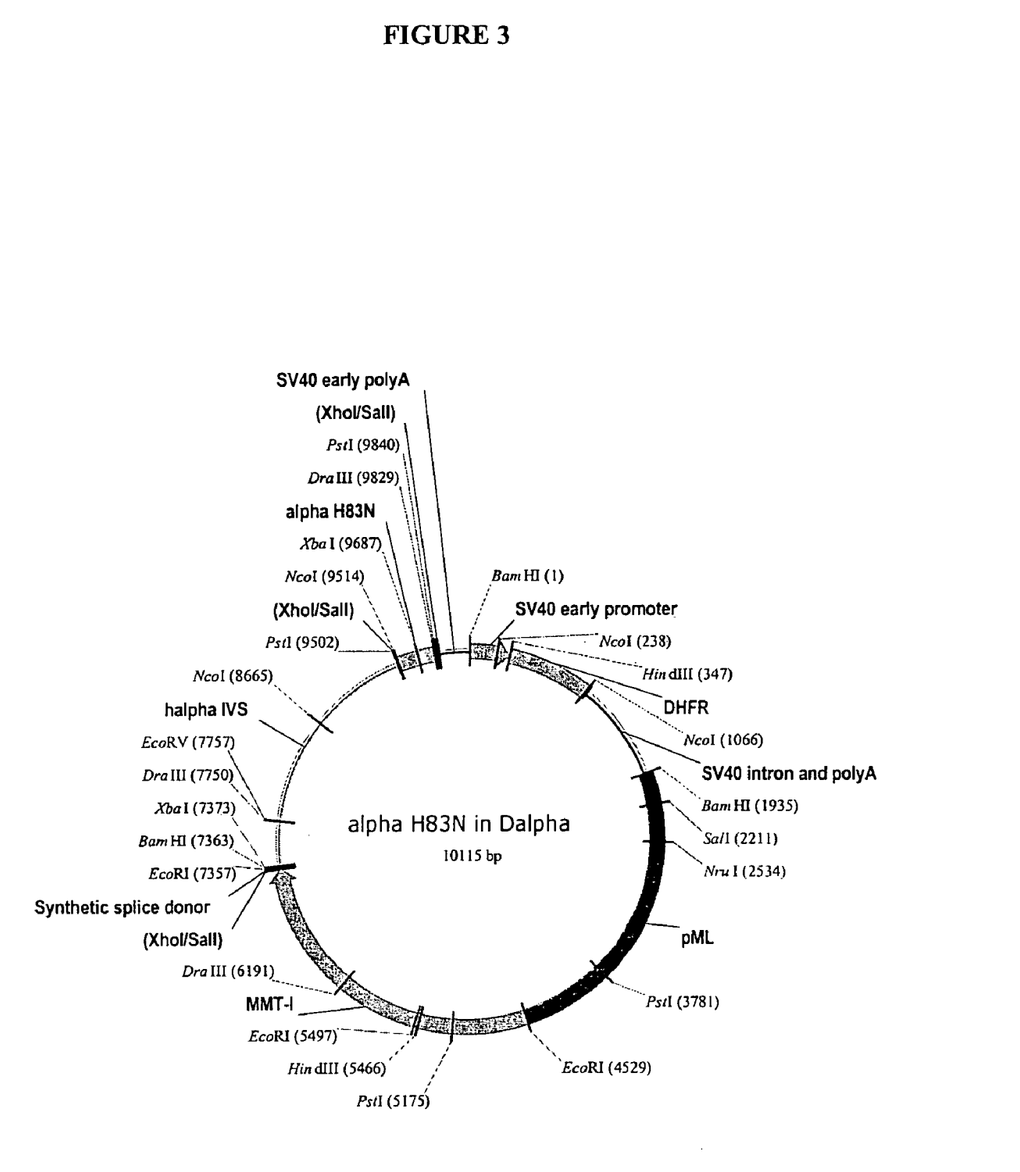
FIG. 3 shows the plasmid map of the expression vector used for the expression of the βE55/V57T subunit.

The αH83N mutant was also subcloned into the Dα vector to yield plasmid p13538, as shown in FIG. 3. The Dα vector is a derivative of pCLH3 AXSV2DHFR. The vector was modified to include a heterologous intron with a synthetic splice donor engineered upstream of the 2 kb XbaI-PstI fragment from intron A of the gonadotropin α subunit gene (containing a splice acceptor). The heterologous intron is situated between the promoter and the XhoI cloning site, placing it in the 5' untranslated region of the RNA transcript. The Dα vector has been described in more detail by Kelton et al., *Mol Cell Endocrinol* 89:141-151 (1992).

Example 4

Expression of Mutant FSH

The GM-1 glycosylation mutant of FSH was first obtained ("GM-1 Lot 1") by cotransfecting p13251 (αH83N) and p13251 (βE55/V57T) to transiently achieve expression of the gonadotropin in serum-free culture medium. For large-scale lipofectamine-mediated transfection (12-24 T175 flasks) CHO-Dukx cells were seeded at $1.3 \times 10^7$ cells/flask in growth medium (MEM a(+), 10% FBS, 1% 1-glutamine) 18-24 h prior to transfection. To transfect cells a lipofectamine 2000/Optimem mix was prepared in bulk (one part in 17.6) and a separate stock of DNA in Optimem was also prepared using the formula 33 mcg of DNA for each subunit (66 mcg in total) per T175 flask Twenty minutes after combining the Optimem/DNA and Optimem/Lipofectamine preparations the DNA/Lipofectamine complexes in Optimem were applied (~10 ml/flask) to recently fed (43.8 ml/flask) cell monolayers. After four to six hours at 37° the cell monolayers were fed 50 ml of growth medium. Approximately 24 h post transfection the cells were transferred to production medium (Sigma CHO PFM supplemented with L-Glutamine or to the Serono-proprietary formulation Sigma CHO PFM C0234). Conditioned production medium was harvested 48 h later.

Example 5

Clones of Mutant FSH

Protoclones

Calcium phosphate co-transfection of CHO-DUKX cells with αH83N in Dα (plasmid #13538) and βE55N/V57T in pCIattR (plasmid #13252) at a ratio of 1:3 was performed using standard methodologies. Protoclones were generated 48 h post transfection by seeding cells in selection medium (MEM α(–), 10% dFBS, 4 mM L-glutamine) at 10,000 cells per well in 96 well plates (Total 1596 wells). After approximately 2 weeks, protoclones were split 1:8 into selection medium containing 0.02 µM MTX. This splitting process was repeated through escalating concentrations of MTX (0.1 µM (192 wells), 0.5 µM, 1.0 µM (116 wells) over the course of 6-8 weeks with 116 protoclones surviving in 1.0 µM MTX.

The 116 protoclones were evaluated for expression by DSL ELISA by using 24 h expression samples from 96 well plates (in 1.0 µM MTX and 10% FBS). Expression levels ranged from off scale low to 3.72 µg/ml. The seventeen highest expressing protoclones were expanded to 24 well plates, to a T25 flask, and then a 3 vial set of each was cryopreserved. The top two protoclones were thawed and expanded for expression confirmation at the T25 scale. GM1-21 and GM1-22 had volumetric productivities of 1.74 and 0.74 µg/ml, respectively with specific productivities of 5.06 and 1.28 pcd, respectively. Based on these results, GM1-21 was chosen for cloning and to produce the second lot of GM-1 in roller bottles as described in Example 6.

Clones

Limiting dilution cloning was initiated by inoculating 96 well plates with 0.25, 0.5, 1.0, and 2.0 GM-1-21 cells/well, respectively. The cloning medium was DMEM/F12 containing 10% cFBS and 1% L-glutamine in the absence of MTX. All wells were examined by microscope and any wells containing multiple cells were eliminated.

After growing approximately 2 weeks, cell populations were expanded to 24 well and, eventually, T25 flasks. Once cells reached 80-100% confluence, volumetric productivities were determined using the DSL FSH ELISA (samples contained 10% FBS). The best 8 clones were expanded to T75 flasks to determine 24 hr volumetric and specific expression. A three vial set of each clone was cryopreserved in DMEM/F12 containing 10% cFBS, 1% L-glutamine, and 10% DMSO. CHO-B1-GM1-21-98 demonstrated volumetric productivity, 7.21 µg/ml with specific productivity of 6.25 pcd. In contrast, CHO-B1-GM1-21-107 demonstrated the highest specific productivity, 7.71 pcd, coupled with 5.81 µg/ml volumetric productivity.

CHO-B1-GM1-21-98 and CHO-B1-GM1-21-107 were expanded to four T175 flasks. At approximately 90% confluence, a pre-MCB (25 vials of each clone) was cryopreserved in DMEM/F12 containing 10% FBS, 1% L-glutamine, and 10% DMSO. GM1-21-98 (passage 7) contained 3.26 million cells per vial and GM1-21-07 (passage 6) contained 6.1 million cells per vial. A vial of each bank was sent to Charles River Laboratories (Malvern, Pa.) for GMP testing. The tests included PTC Mycoplasma, Sterility, MAP with LCMV Challenge Testing, HAP testing, Extended In Vitro Focus Induction Assay for Xenotropic Murine Leukemia Virus, Extended XC Plaque Assay for Murine Leukemia Virus, and Isoenzyme Analysis, with each passing all tests.

Example 6

Additional Expression of Mutant FSH

GM-1 was produced by growing Protoclone GM1-21 described in Example 5 in two 850 cm² roller bottles ("GM-1 Lot 2"). The volume of serum-free production medium (DMEM-F12+IFCS) conditioned in this run was 2600 ml. A small quantity (13 mls of concentrated culture supernatant containing approximately 0.2 mg GM-1) remains in –80° C. storage at SRBI because a 36 ml aliquot of the concentrated culture supernatant was lost during a dialysis transfer. Quantification was by DSL Active® FSH ELISA using the conversion 1IU=138 ng FSH.

Example 7

Purification of Mutant FSH

Sample Preparation

Production media containing mutant FSH was harvested and filtered using 0.22 μm filter units and frozen at −70° C. The target proteins in media were thawed overnight at 4° C., and concentrated by ultrafiltration using Ultrasette Screen Channel TFF device, 10 K Omega membrane, P/N 0S010C70, by Pall Life Science. The retentate was recovered and dialyzed overnight versus 0.1 M Tris, pH 7.4 containing 0.5 M NaCl, 3×5 Liters. The dialyzed protein was recovered, 0.22 μm filtered, and was purified immediately or stored at −70° C. until purified.

Immunoaffinity Purification

Glycosylation mutant GM-1 was purified by anti FSH immunoaffinity resin B5 (Serobio) containing 2.2 mg anti-FSH antibody per ml of resin. A 10.2 ml bed volume was prepared in 1.5 cm×10 cm OmniFit column. The resin was pre equilibrated with 0.1 M Tris, pH 7.4 containing 0.5 M NaCl. The dialyzed crude protein was loaded at one ml/min. The column was washed sequentially with the five column volumes of 0.1 M Tris, pH 7.4 containing 0.5 M NaCl, five column volumes of 100 mM ammonium bicarbonate, pH 7.6, and the target protein eluted with 18-20 column volumes of 1 M $NH_4OH$. The fractions containing the eluted protein were pooled, neutralized with glacial acetic acid, and concentrated by ultrafiltration with Amicon stirred cell using Amicon YM 10 membrane. The retentate was dialyzed in Pierce Snakeskin dialysis tubing, 10 K MWCO, versus 4×5 liters of water over 24 hours. The dialyzed protein was recovered and concentrated by Centriprep YM 10 to decrease the volume to approximately one ml.

Characterization

The apparent recovery of purified protein GM-1 through this single step immunoaffinity process is 31.4-52.9% at 73.8 to 80.6% heterodimer purity with protein concentration determined by amino acid composition analysis and formula weight originally estimated as 35,000 Da from the MALDI-TOF glycoform distribution of subunits.

Identity of the protein was confirmed by N-terminal peptide sequencing. All N-terminal sequences that could be identified in GM-1 reflect termini of either the α-subunit or β-subunit of FSH. Although the identity of a single low-abundance protein band visible by silver staining could not be established, the data remain consistent with ±80% subunit purity.

Example 8

Morphology of Mutant FSH

Figure 4:
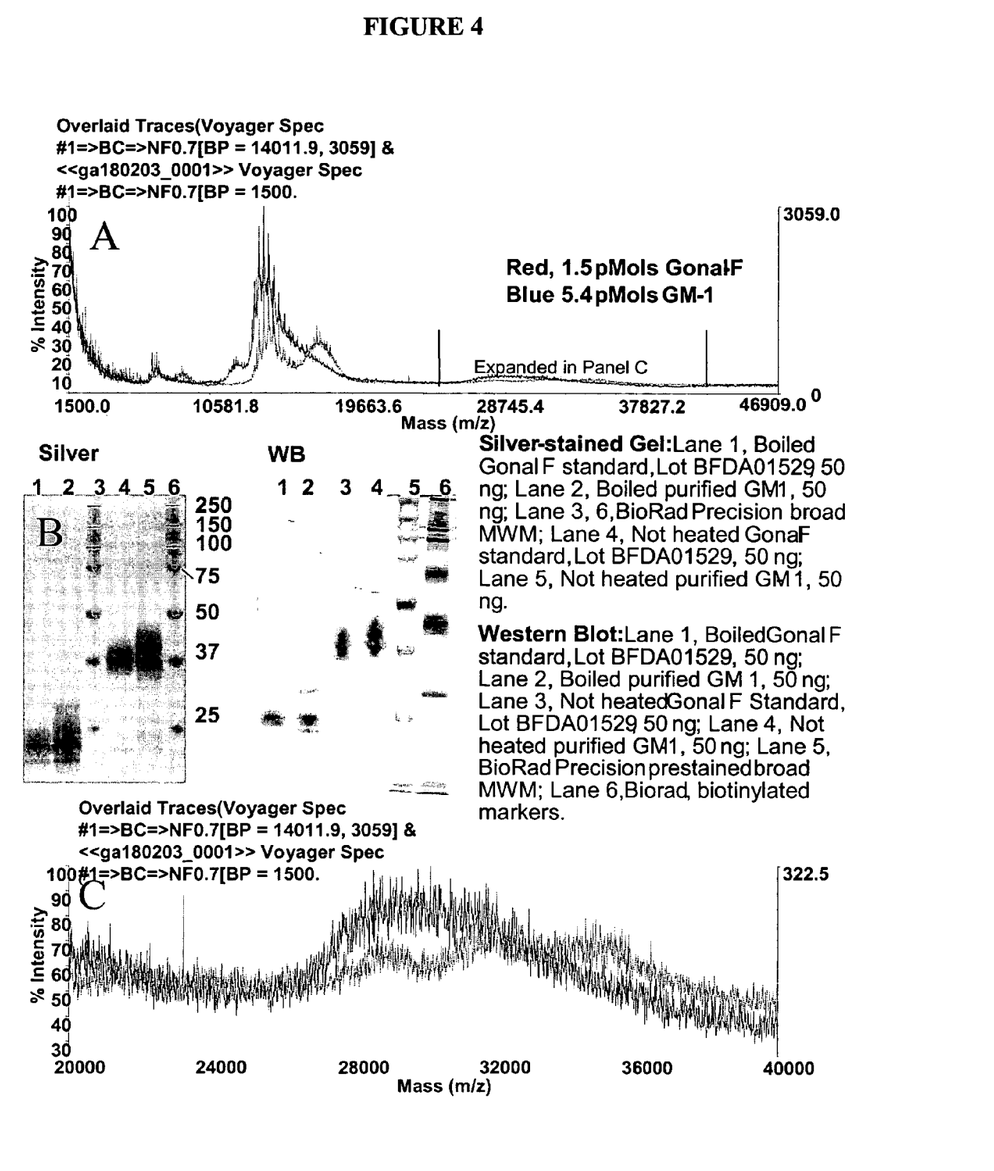
FIG. 4 shows the morphology of GM-1. Panel A and C: MALDI-TOF mass spectrometry performed on GM-1 and Gonal-F. Panel B: LDS-PAGE analysis of GM-1 and Gonal-F.

To determine the glycoform distribution of the purified protein, MALDI-TOF mass spectrometry was performed on GM-1 and Gonal-F. The mass spectra analysis shown in FIG. 4A shows a 26% increase in relative abundance of the mass classes that contain hyperglycosylated forms in GM-1 relative to Gonal-F where they contain 36.8% of the total subunit glycoforms as opposed to 29.2% of the subunit glycoforms in Gonal-F. The difference between Gonal F and GM-1 MALDI-TOF mass spectra is consistent with the shifts in apparent molecular weight distributions of subunit and heterodimer seen by silver-stained PAGE and western blotting (FIG. 4B).

Under the conditions of MALDI-TOF mass spectrometry GM-1 appears to preferentially retain αβ heterodimer conformation in FIG. 4C, in contrast to the random distribution of αα, αβ and ββ dimers seen Gonal F. This suggests GM-1 dissociates less than Gonal-F under MALDI-TOF sample preparation conditions and is consistent with attributing the possibility of higher thermodynamic or kinetic stability to the GM-1 heterodimer. A model of GM-1 glycosylation was calculated as the binomial distribution of random occupancy of six sites by biantennary, fucosylated, disialylated glycoforms without classes for fully non-glycosylated subunits and was compared with the observed mass spectra. The results indicate higher than predicted occupancy (0.021, vs 0.0) of the extreme class (α0), lower occupancy (0.095 vs 0.214) occupancy of the (α1 or β0) class, higher (0.516 vs 0.428) occupancy of the (α2 or β1) class, higher (0.312 vs 0.285) occupancy of the (α3 or β2) class and lower occupancy (0.056 vs 0.071) of the β3 class.

Example 9

Analysis of Mutant FSH

In Vitro Binding of Mutant FSH

The efficacy of GM-1 Lot 1 and GM-1 Lot 2 was determined in an FSHR cAMP assay. Large batches of CHO cells line which recombinantly express human FSH receptor or human LH receptor were grown and disrupted by nitrogen cavitation (20 min equilibration to 900 psi, followed by rapid pressure release) in 0.025 M Tris pH 7.4 containing 0.25 M sucrose, 10 mM $MgCl_2$, 1 mM EDTA and one part per thousand Sigma Protease Inhibitor cocktail (p8350). Following preliminary clarification (10 min×1000×g at 4° C.) the membranes fraction was pelletted (60 min×100,000×g×4° C.) by ultracentrifugation. The membranes fraction was resuspended in binding buffer (0.01 M Tris pH 7.4 containing 5 mM $MgCl_2$), protein concentration estimated by Bradford (BioRad) protein assay and stored frozen at −80° C. for future use. Typically 15 μg of membrane protein appropriately bearing FSHR or LHR was analyzed, per well, in competition assays.

Radioligand binding was evaluated in 96 well plates, 100 μl/sample well. The assay buffer was 0.01 M Tris pH 7.4 containing 5 mM $MgCl_2$ and 0.1% BSA and 0.3 nM $^{125}I$-hCG (for LHR) or 0.4 nM $^{125}I$-FSH (for FSHR). Competing GM-1 was diluted with assay buffer and mixed with radiolabelled ligand prior to the addition of receptor-bearing membranes. Nonspecific binding was determined in the presence of 500 nM unlabeled hCG or FSH. Binding was allowed to equilibrate for 90 min at 37° C. with shaking. Binding assays were terminated by filtration through a low protein binding durapore membrane (Millipore Multiscreen) pre-incubated in assay buffer. Filter wells were washed three times with ice cold binding buffer (BSA-free assay buffer), dried, and punched out. Bound radioactivity was measured in an HP Cobra II gamma counter using a pre-programmed detection window specific for $^{125}I$ emission. Data were analyzed using a single site model and Graph Pad Prizm software.

In Vitro Function of Mutant FSH

The function of GM-1 Lot 1 and GM-1 Lot 2 was determined by measuring dose response curves of cAMP production in the gonadotropin receptor-transfected CHO cells described above. The release qualification data for two lots of each lead protein is compiled in Table 3 below:

TABLE 3

In vitro function and receptor binding characteristics of GM-1

| Protein/Lot | FSHR EC$_{50}$ | FSHR K$_i$ |
| --- | --- | --- |
| GM-1/1 | $61.2 \pm 4.5 \times 10^{-12}$ M | $1.9 \pm 0.3 \times 10^{-9}$ M |
| GM-1/2 | $20.9 \pm 2.0 \times 10^{-12}$ M | $2.3 \pm 0.6 \times 10^{-9}$ M |

Example 10

Stability of Mutant FSH

A three month stability study of the stability of GM-1 bioactivity was performed by maintaining a sterile aliquot of GM-1 at 4° C. for three months. The GM-1 in that aliquot was sampled and tested in the FSHR cAMP assay at times zero, seven days, 32 days and 91 days. Under the conditions of this study the EC50 of GM-1 changed less than two fold during 91 days storage at 4° C. These data indicate the bioactivity of GM-1 stored at 4° C. is stable for up to three months.

Example 11

Activity of Mutant FSH

Figure 5:
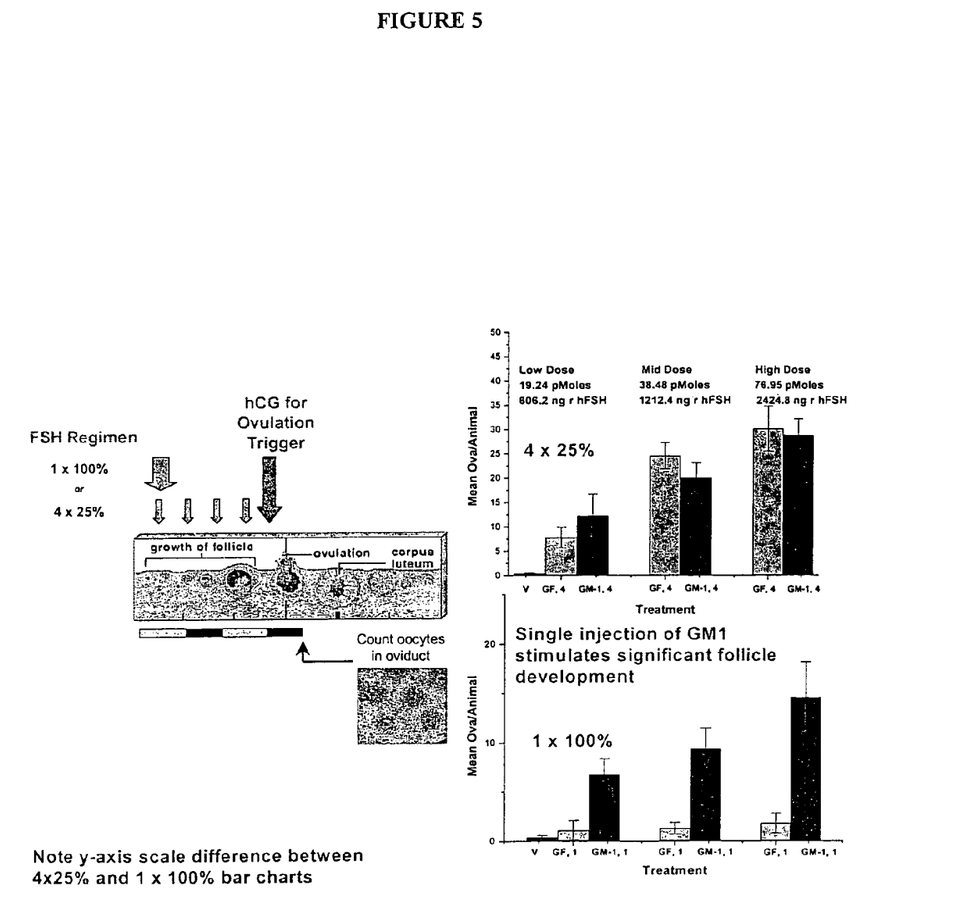
FIG. 5 shows the performance of GM-1 in the immature rat two-day ovulation induction model.

FIG. 5 shows the performance of GM-1 in the immature rat two-day ovulation induction model. Administered as a single dose, recombinant hFSH failed to evoke an ovulatory response while GM-1 was able to do so. Moreover, performance of GM-1 in the standard Steel-man Pohley ovarian weight gain assay was comparable to that of Gonal-F (data not shown).

The doses tested in FIG. 5 correspond to 6, 12 and 24 IU FSH. When FSH-CTP (Organon 36286) was tested in this model at the single dose, 10 IU, with three dose regimens (4×25%, 2×50% and 1×100%) the mean numbers of ovaries observed per animal were 16.3±3.8, 19.1±3.6 and 21.5±3.9, respectively (data not shown). From the data above 12 IU GM-1 administered 1×100% evoked the mean ovulatory response 9.4±2.1 ova per animal (6.8±1.6 ova/animal at 6 IU and 14.6±3.6 ova/animal at 24 IU). The data are consistent with the possibility that GM-1 may be more respectful of "mono-ovulation" or more controllable by manipulation of the dosing regimen.

The invention claimed is:

1. A recombinant FSH, wherein the FSH alpha subunit comprises the sequence of SEQ ID NO. 3, and wherein the FSH beta subunit comprises the sequence of SEQ ID NO. 4, and wherein said recombinant FSH has an increased in vivo half-life compared to wild type FSH.

2. The recombinant FSH of claim 1, wherein N83 of the alpha subunit is glycosylated, wherein N55 of the beta subunit is glycosylated, and wherein T57 of the beta subunit is glycosylated.

3. A cell comprising a first vector comprising DNA encoding an FSH alpha subunit comprising the sequence of SEQ ID NO. 3 and a second vector comprising DNA encoding an FSH beta subunit comprising the sequence of SEQ ID NO. 4.

4. The cell of claim 3, wherein the first and second vectors are expression vectors.

5. The cell of claim 4, wherein the cell is a mammalian cell.

6. A method for producing an FSH mutant comprising:
(a) providing mammalian cells, wherein the cells comprise a first expression vector and a second expression vector; and
(b) inducing expression of the FSH mutant, wherein the first expression vector encodes the FSH alpha subunit comprising the sequence of SEQ ID NO. 3 and wherein the second expression vector encodes the FSH beta subunit comprising the sequence of SEQ ID NO. 4.

7. The method of claim 6, wherein the cells are capable of glycosylating proteins.

8. A composition comprising the recombinant FSH of claim 2 and a pharmaceutically acceptable carrier or excipient.

9. A method of treating an infertile mammal, comprising administering to a mammal in need thereof an effective amount of the recombinant FSH mutant according to claim 2.

10. A method of stimulating folliculogenesis in a mammal, comprising administering to a mammal in need thereof an effective amount of the recombinant FSH mutant according to claim 2.

11. A method of inducing ovarian hyperstimulation in a mammal, comprising administering to a mammal in need thereof an effective amount of the recombinant FSH mutant according to claim 2.

12. The recombinant FSH of claim 1 wherein N55 of the beta subunit is glycosylated.

* * * * *